United States Patent
Yost et al.

(10) Patent No.: US 6,740,048 B2
(45) Date of Patent: May 25, 2004

(54) NON-INVASIVE METHOD OF DETERMINING DIASTOLIC INTRACRANIAL PRESSURE

(75) Inventors: William T. Yost, Newport News, VA (US); John H. Cantrell, Jr., Williamsburg, VA (US); Alan R. Hargens, San Diego, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/263,285

(22) Filed: Sep. 25, 2002

(65) Prior Publication Data

US 2003/0191410 A1 Oct. 9, 2003

Related U.S. Application Data

(60) Provisional application No. 60/371,601, filed on Apr. 8, 2002.

(51) Int. Cl.[7] ................................................ A61B 5/00
(52) U.S. Cl. ........................................ 600/561; 600/300
(58) Field of Search ................................. 600/300, 301, 600/407, 437, 438, 449, 451, 561, 587

(56) References Cited

U.S. PATENT DOCUMENTS

| | | | |
|---|---|---|---|
| 4,971,061 A | 11/1990 | Kageyama et al. | |
| 5,214,955 A | 6/1993 | Yost et al. | |
| 5,388,583 A * | 2/1995 | Ragauskas et al. | 600/451 |
| 5,617,873 A * | 4/1997 | Yost et al. | 600/561 |
| 5,591,476 A | 9/1999 | Beach | |
| 6,117,089 A * | 9/2000 | Sinha | 600/561 |
| 6,146,336 A * | 11/2000 | Paulat | 600/561 |
| 6,210,346 B1 | 4/2001 | Hall et al. | |
| 6,231,509 B1 | 5/2001 | Johnson et al. | |
| 6,264,611 B1 | 7/2001 | Ishikawa et al. | |
| 6,413,227 B1 | 7/2002 | Yost et al. | |
| 6,475,147 B1 * | 11/2002 | Yost et al. | 600/438 |
| 6,589,189 B2 * | 7/2003 | Meyerson et al. | 600/561 |
| 2003/0171693 A1 | 9/2003 | Yost et al. | |
| 2003/0191409 A1 | 10/2003 | Yost et al. | |
| 2003/0191411 A1 | 10/2003 | Yost et al. | |

FOREIGN PATENT DOCUMENTS

| | | |
|---|---|---|
| WO | WO 00/68647 | 11/2000 |

\* cited by examiner

*Primary Examiner*—Eric F. Winakur
*Assistant Examiner*—Patricia C. Mallari
(74) *Attorney, Agent, or Firm*—Helen M. Galus

(57) ABSTRACT

A method is presented for determining diastolic intracranial pressure (ICP) in a patient. A first change in the length of a path across the skull of the patient caused by a known change in ICP is measured and used to determine an elasticity constant for the patient. Next, a second change in the length of the path across the patient's skull occurring between systolic and diastolic portions of the patient's heartbeat is measured. The patient's diastolic ICP is a function of the elasticity constant and the second change.

20 Claims, 3 Drawing Sheets

NON-INVASIVE METHOD OF DETERMINING DIASTOLIC INTRACRANIAL PRESSURE

CLAIM OF BENEFIT OF PROVISIONAL APPLICATION

Pursuant to 35 U.S.C. Section 119, the benefit of priority from provisional application 60/371,601, with a filing date of Apr. 8, 2002, is claimed for this non-provisional application.

ORIGIN OF THE INVENTION

The invention described herein was made by employees of the United States Government and may be manufactured and used by or for the Government for governmental purposes without the payment of any royalties thereon or therefor.

CROSS-REFERENCE TO RELATED APPLICATIONS

This patent application is co-pending with one related patent application entitled "NON-INVASIVE METHOD OF DETERMINING ABSOLUTE INTRACRANIAL PRESSURE" (NASA Case No. LAR 16510-1), by the same inventors as this patent application.

BACKGROUND OF THE INVENTION

1. Field of the Invention

This invention relates to determination of intracranial pressure. More specifically, the invention is a non-invasive method for determining the diastolic intracranial pressure in a patient.

2. Description of the Related Art

Bone tissue is the most rigid of all animal tissues. The skull bone surrounds and protects one's cranial complex which includes the brain and cerebrospinal fluid (CSF) surrounding the brain. The human brain and the spinal cord are immersed in CSF which is continuously generated and reabsorbed by the body. The CSF is contained in a membrane covering the inside of the skull and the spinal cord which terminates in a sack located at the sacrum. The brain and the membrane containing the CSF also contain blood vessels, which are in direct communication with the CSF and add to the total volume of the cerebrospinal system. The blood volume in these blood vessels varies rhythmically with the heartbeat thereby causing corresponding oscillations in the intracranial pressure (ICP). The collective compliance (i.e., the ability to increase in volume with increasing pressure) of the skull and CSF is too small to accommodate the pressure regulation needed for proper circulation of blood within the brain and spinal cord. Hence, pressure within the cranial complex is controlled by the compliance of the brain's venous bed in association with the creation and removal of CSF by specialized structures within the brain.

Pressure is regulated by rate of production of CSF by the choroid plexus, and rate of removal of cerebrospinal fluid by the arachnoid villi. These rates therefore play a crucial role in blood flow regulation, while also relating to disease and pathologies which can occur. A complex interaction between the blood vessels and ICP accomplishes the needed regulation of blood flow in brain tissue.

Substantial effort has been devoted to understanding the dynamics of pulsatile effects on ICP. Towards this end, many investigators have developed an "equation of state" which describes pressure and volume relationships in the cranial complex. While the various relationships differ, it is generally accepted that increases in diastolic ICP (i.e., increases in ICP occurring during the diastolic rhythm of one's heartbeat) generate intracranial hypertension that affects the viability and function of the human brain.

Given the above, monitoring of diastolic ICP is of significant diagnostic and post-operative importance for patients with cranial injuries, pathologies or other conditions that may affect the pressure of the subarachnoidal fluid around the brain, and for patients who have undergone brain surgery. In general, ICP has traditionally been measured and monitored by means of a pressure sensor inserted through the skull into the brain. Usually a hole is drilled in the skull and a catheter with a pressure sensor is inserted into the brain fluid. This known procedure, while simple and accurate is not suitable for long-term monitoring because an open wound must be maintained in the skull. Antibiotics are only partially effective in treating cranial infections so the pressure sensor can only be left in place for two weeks or less.

Long-term monitoring of ICP is currently achieved by implanting a pressure sensor and transmitter into the brain. The ICP is thereafter monitored by means of a receiver located outside the skull. However, this solution is not preferred because it includes the risks associated with implanting anything in the brain, and because of the problems associated with providing power to an implanted transmitter.

A variety of non-invasive systems and/or methods of measuring relative changes in ICP have been described in each of U.S. patent application Ser. Nos. 09/459,384, 09/493,044, 10/094,023, and 10/121,932. However, none of these provide for the measurement or determination of a diastolic ICP.

SUMMARY OF THE INVENTION

Accordingly, it is an object of the present invention to provide a method of determining diastolic ICP in a non-invasive fashion.

Another object of the present invention is to provide a method of determining diastolic ICP that minimizes the number of procedures used.

Other objects and advantages of the present invention will become more obvious hereinafter in the specification and drawings.

In accordance with the present invention, a method is presented for determining diastolic intracranial pressure (ICP) in a patient. A first change in the length of any path across the skull of the patient caused by a known change in ICP is measured. This first change relative to the known change in ICP is indicative of an elasticity constant for the patient. Next, a second change in the length of the path across the patient's skull occurring between systolic and diastolic portions of the patient's heartbeat is measured. The patient's diastolic ICP is a function of the elasticity constant for the path and the second change in the length of the path across the patient's skull.

DETAILED DESCRIPTION OF THE INVENTION

Figure 1:
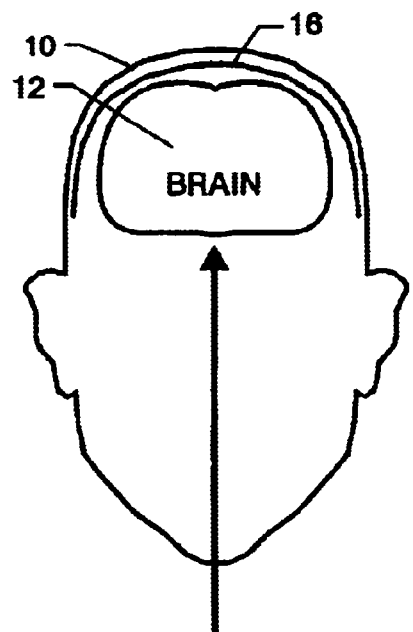
FIG. 1 is a schematic view of the skull and brain of a patient with the brain being coupled to the patient's heart.
Figure 3:
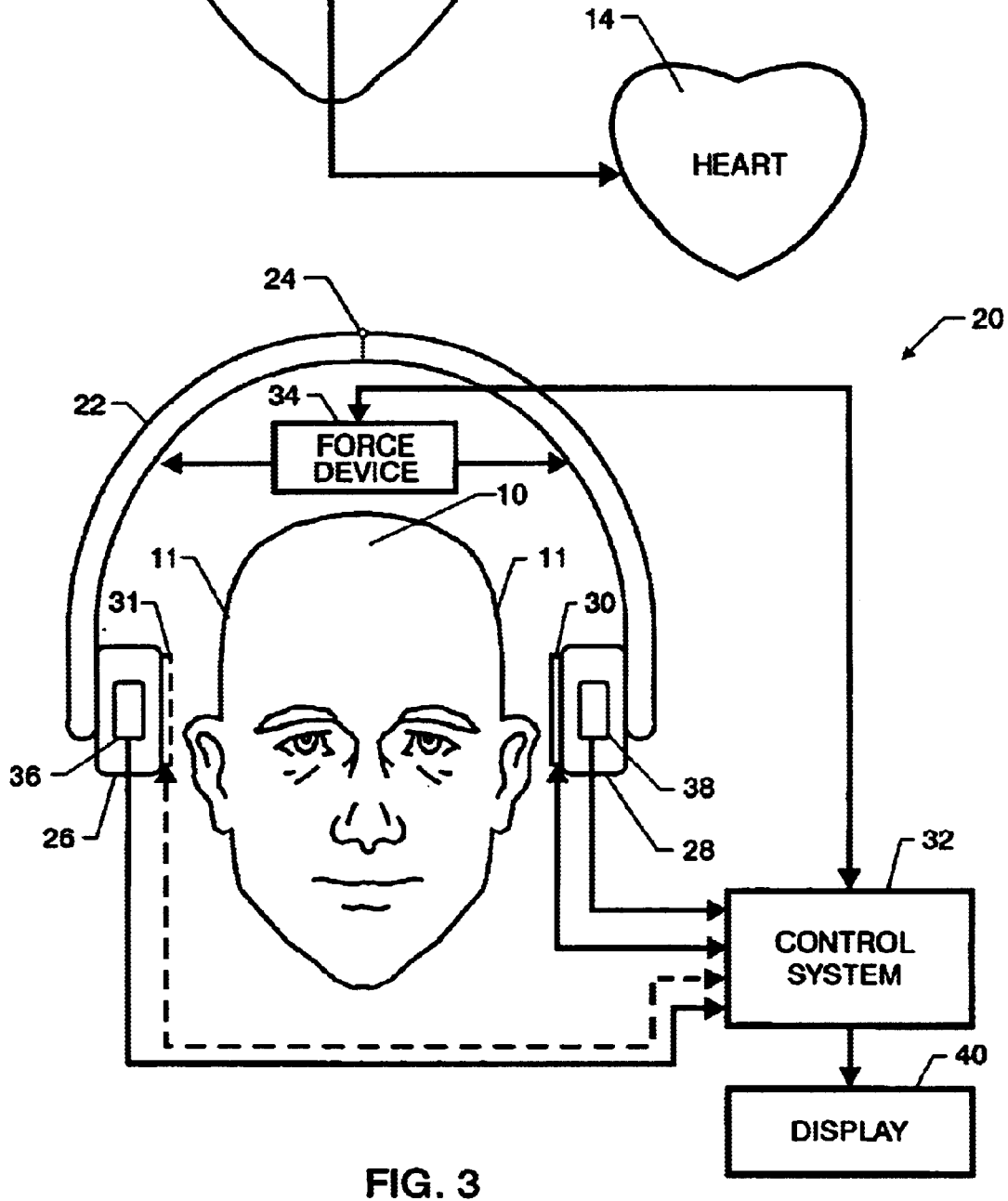
FIG. 3 is a schematic view of a system that can be used to measure/monitor skull expansion in a patient for use by the method of the present invention.

Referring now to the drawings, and more particularly to FIG. 1, a patient's skull 10 is illustrated with his brain referenced by numeral 12. As is well known, brain 12 is a venous structure that is coupled to the patient's heart 14 and, therefore, undergoes systolic-diastolic changes in blood pressure. Surrounding brain 12 is the patient's cerebrospinal fluid (CSF) 16, the pressure of which is known as intracranial pressure or ICP as it will be referenced herein.

Skull 10 tends to expand and contract with changes in ICP. However, the compliance (i.e., the ability of skull 10 to expand with increasing ICP) of skull 10 is not sufficient to accommodate the pressure regulation needed for proper circulation of blood within brain 12 and the patient's CSF system (not shown). Accordingly, pressure within skull 10 is controlled by compliance of the brain's venous bed in association with the addition/removal of CSF 16.

Figure 2:
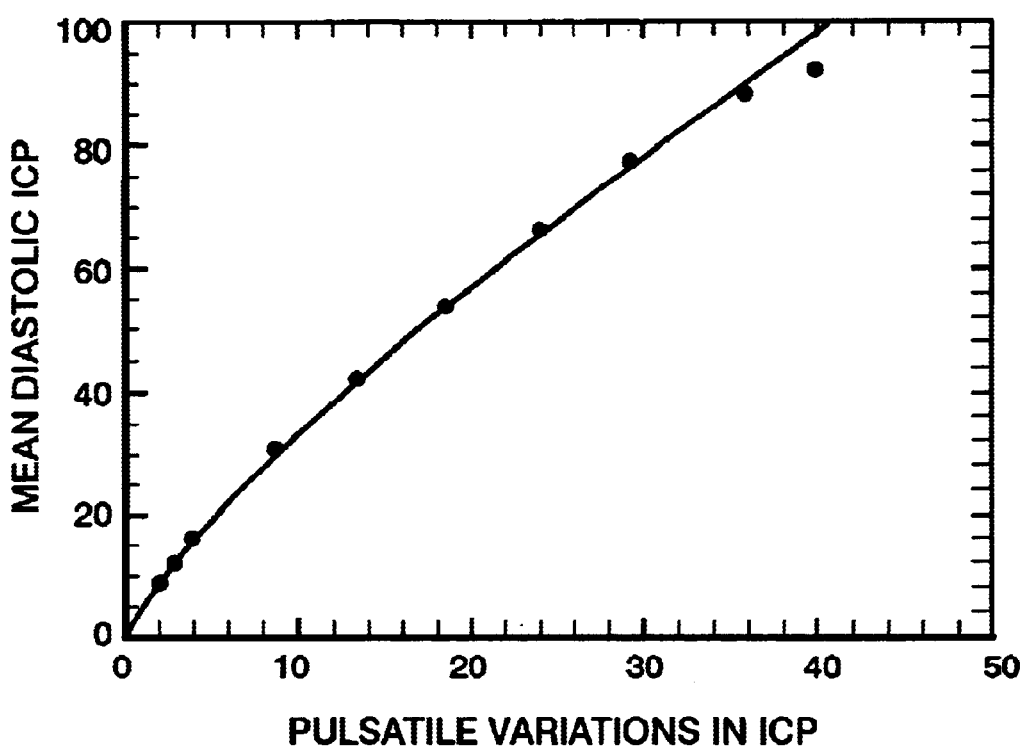
FIG. 2 is a graphical view of a model relating pulsatile variations in ICP to the mean diastolic ICP for a typical human CSF system.

As mentioned above, substantial effort has been devoted to understanding the dynamics of pulsatile effects of ICP. The present invention makes use of a hydrodynamic model that describes a numerical relationship between pulsatile variations in ICP (i.e., difference between systolic ICP and diastolic ICP) and a mean diastolic ICP. The hydrodynamic model is described in detail by Mauro Ursino in "A Mathematical Study of Human Intracranial Hydrodynamics Part 1-The Cerebrospinal Fluid Pulse Pressure," Annals of Biomedical Engineering, Volume 16, pages 379–401, 1988, which article is incorporated herein by reference as if set forth in its entirety. The graphical version of the hydrodynamic model relating the pulsatile variations in ICP to the mean diastolic ICP is shown for a general human population in FIG. 2 herein. When a best-fit curve is applied to the values in FIG. 2, a power law relationship between pulsatile variations in ICP and a mean diastolic ICP can be written mathematically as $$ICP_{DIAS} = A(K\Delta x)^B \quad (1)$$

where $ICP_{DIAS}$ is diastolic ICP for a patient at a measurement point in time, K is an elasticity constant to be determined for the patient by the present invention, $\Delta x$ is the amount of linear skull expansion (i.e., path length change) occurring (at the "measurement point in time") between the systolic and diastolic points in the heartbeat of the patient, and A and B are constants determined from a best fit to the general population data in FIG. 2. For example, for the curve illustrated, A is 5.6957 and B is 0.77312. However, it is to be understood that some variation in A and B will occur depending on the "best-fit curve" used. Accordingly, particular choices for A and B are not limitations of the present invention.

In addition to the above-cited work by Ursino, the present invention takes note of the fact that the skull responds to pulsatile changes in ICP with a very slight increase in volume referred to hereinafter as pulsatile skull expansion, i.e., the amount of skull expansion between the systole and diastole portions of a heartbeat. The volume change resulting from pulsatile skull expansion can be viewed as a change in path length measured, for example, across the skull.

The elasticity constant K for a given patient can be determined in accordance with $$K = \Delta ICP/\Delta l \quad (2)$$

where $\Delta ICP$ is a static ICP change caused by a manipulation of the patient and $\Delta l$ is the resultant skull expansion associated therewith. The resultant skull expansion $\Delta l$ is viewed herein as a change in path length measured, for example, across the skull. Once the elasticity constant K is established for a given patient, equation (1) provides for the determination of the mean diastolic ICP or $ICP_{DIAS}$ using a measurement of pulsatile skull expansion $\Delta x$ which will be explained further below.

Before describing the details of the method of the present invention, it is to be understood that the inducement of changes in ICP and/or the measurement of changes in ICP can be carried out in a variety of ways without departing from the scope of the present invention. For example, intentionally induced changes in ICP can be brought about by mechanical manipulation of the patient (e.g., pressure applied to the skull, through the use of a tilt bed, immersion of the patient in a negative pressure chamber, etc.) or by chemical manipulation of the patient (e.g., giving the patient drugs to alter blood gas concentration, decrease production of CSF, increase the uptake rate of CSF, etc.). Changes in ICP can be measured/determined by a variety of acoustic systems (e.g., pulse-echo, pitch-catch, etc.) such as the constant frequency pulsed phase locked-loop ultrasonic measuring system described in U.S. Pat. No. 5,214,955, which patent is incorporated herein by reference as if set forth in its entirety.

By way of a non-limiting example, FIG. 2 illustrates a system 20 that can be used to determine elasticity constant K and monitor pulsatile skull expansion $\Delta x$ of a patient. System 20 includes an adjustable headband 22 hinged at its central portion as indicated by dashed line 24. Pressure pads 26 and 28 are positioned at either end of headband 22 such that, when headband 22 is fitted over a patient's skull 10, pressure pads 26 and 28 are positioned at approximately diametrically opposed positions about skull 10. Each of pressure pads 26 and 28 can define a conforming pad (e.g., a gel-filled pad) to assure uniform contact with skull 10.

Mounted to pressure pad 28 is a transducer 30 capable of transmitting and receiving acoustic signals for use in a pulse-echo measurement approach. Signals are provided to transducer 30 by a control system 32 and acoustic echoes received by transducer 30 are provided to control system 32. In the pulse-echo approach, pressure pad 26 can be constructed as an anechoic chamber to reduce reflections from the skin air interface adjacent the side of the skull subjected to the acoustic signals. Separate transmission and reception transducers could also be used for either pulse-echo or pitch-catch measurement approaches. For example, in terms of a pitch-catch measurement approach, transducer 30 could be a dedicated transmitter and a transducer 31 (shown in phantom) could be a dedicated receiver mounted on pad 26.

A force device 34 is coupled to headband 22 on either side of hinge 24. Force device 34 is any controllable device capable of drawing headband 22 together about hinge 24 such that an increasing pressure is applied to skull 10 via each of pads 26 and 28. Examples of force device 34 can include, but are not limited to, solenoids, screw drives, hydraulic drives, gear drives, etc., where system response is linear. That is, force device 34 should be "linear" in its expansion and contraction characteristics as it follows skull expansion. Such linearity is manifested by a force device having a constant (i.e., linear) and known stiffness (or modulus).

Control of force device 34 can be maintained by control system 32 which can be entirely automatic or can include means for accepting manual inputs. To monitor the amount of pressure applied to skull 10, pressure sensors 36 and 38 can be provided at each of pressure pads 26 and 28, respectively. The pressure readings can be used by control system 32 as a feedback control for force device 34. Pressure outputs can also be displayed on a display 40.

To monitor skull expansion using the pulse-echo approach, headband 22 is placed on skull 10 such that pads 26 and 28 are in contact with the patient's skin 11 adjacent to skull 10. With respect to pad 28, note that transducer 30, as well as portions of pad 28 to the sides of transducer 30, will contact skin 11. This ensures good coupling of acoustic signals transmitted into skull 10 from transducer 30 as well as good coupling of acoustic signal reflections from skull 10 to transducer 30.

In general, system 20 monitors skull expansion in accordance with the teachings of U.S. Pat. No. 5,214,955. That is, system 20 measures path length changes as a function of phase difference between the acoustic signal transmitted into skull 10 and the acoustic signal measured at a detection location at two different points in time. As mentioned above, the detection location can be: i) the same as the transmission location when a single transmission/reception transducer 30 is used, ii) adjacent the transmission location if a dedicated reception transducer is mounted adjacent transducer 30, iii) at another location that is spaced apart from the transmission location, e.g., at a location diametrically-opposed to the transmission location as would be the case if dedicated reception transducer 31 were used.

Prior to monitoring skull expansion using system 20, it may be desirable to establish and apply a differential pressure bias to skull 10 at each of the transmission, reception and, if applicable, reflection locations about skull 10 in order to reduce or eliminate the effects associated with pulsatile blood perfusion, i.e., the small amount of systolic diastolic blood located between the patient's skin and skull. The amount of differential pressure required to reduce or eliminate the influence of pulsatile blood perfusion can be determined by monitoring skull expansion as a function of applied differential pressures. Initially, the slope of a plot of these two parameters will be fairly steep. However, the slope will level off to a constant once the effects of pulsatile blood perfusion are reduced/eliminated. Note that this step is not required if acoustic signals can be coupled directly to/from the skull as opposed to indirectly through the patient's skin.

The effects of blood perfusion may be reduced or eliminated as described above. Then, the patient (with headband 22 still in place) is "manipulated" to bring about known changes in ICP without a corresponding change in pulsatile blood perfusion. Such manipulations can be mechanical or chemical in nature. Mechanical manipulations can include the use of additional pressure being applied by force device 34 of system 20, the use of a tilt bed while system 20 maintains its differential pressure bias, the immersion of the patient in a negative pressure chamber, etc. Chemical manipulations include drug intervention techniques for increasing/decreasing ICP.

Figure 4:
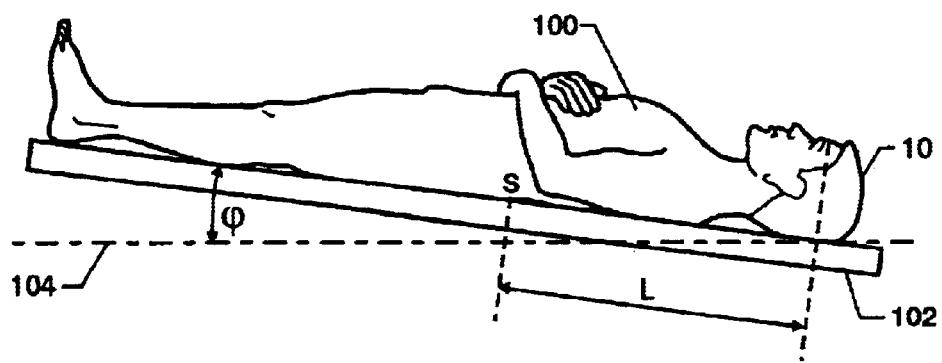
FIG. 4 is a side view of a patient lying in a supine position on a tiltable bed for mechanical manipulation of the patient as a means to induce/cause known changes in intracranial pressure (ICP) in the patient.

As a result of such patient manipulations, known changes in ICP (or $\Delta$ICP) are brought about while corresponding changes in skull expansion (or $\Delta$l) are monitored. The causing of known changes in ICP can be brought about by the tilt bed/angle method, which has been described in U.S. Pat. No. 5,617,873. Briefly, as shown in FIG. 4, a patient 100 lies supine on a tiltable bed 102. Note that while system 20 would remain coupled to patient 100, it has been omitted from FIG. 4 for clarity of illustration. With bed 102 tilted by an angle $\phi$ with the legs of patient 100 higher than skull 10, a change (increase in this case) in ICP (or $\Delta$ICP) is given as $$\Delta ICP = \rho g L \sin \phi \qquad (3)$$

where $\rho$ is the mass density of spinal fluid, g is the earth's gravitational constant, L is the distance from the center of the patient's sacrum (the location of which is indicated at S) to the center of skull 10, and $\phi$ is the amount of tilt angle of bed 102 relative to a (horizontal) datum 104. The present invention is not limited to a measurement of L that originates at the patient's sacrum. For example, L could be measured with respect to another reference point such as the point at which pressure in the spinal column does not change with tilt angle. Thus, for any given patient with a known/measurable distance L, $\Delta$ICP can be calculated using equation (3).

As mentioned above, changes in skull expansion measured by system 20 are essentially defined by changes in path length $\Delta$l that the acoustic signal travels between its transmission and reception locations. That is, between any two measurement points in time, the path length "l" that the acoustic signal travels gets longer in the case of positive skull expansion or shorter in the case of negative skull expansion (i.e., skull contraction). Path length l could be defined by one or more paths across skull 10 depending on the number of such lengths traversed by the acoustic signal between its transmission and reception locations. Thus, the change in path length $\Delta$l is measured between the two points in time defined by the start of the "manipulation" causing the change in ICP and the completion of the "manipulation." For example, using the tilt bed method, $\Delta$l would be the change occurring between first and second angular positions of the tilt bed. Using the known change $\Delta$ICP and the corresponding path length change $\Delta$l, the elasticity constant K is determined in accordance with equation (2).

Figure 5:
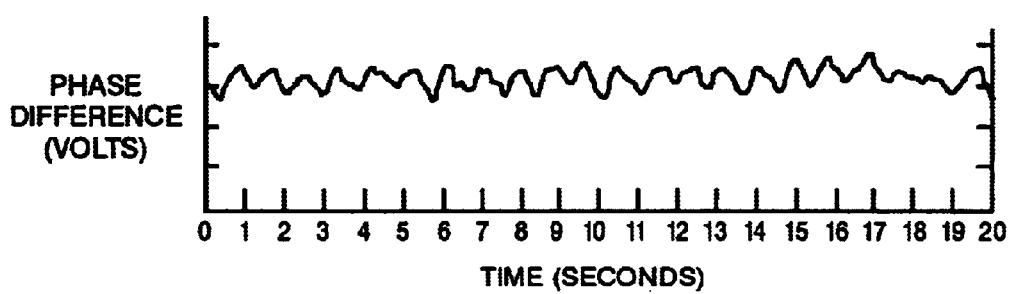
FIG. 5 is a graph of a patient's pulsatile skull expansion versus time as measured by, for example, the system in FIG. 3.

With elasticity constant K now being known, the present invention need only measure pulsatile skull expansion $\Delta$x and use equation (1) to determine diastolic ICP or $ICP_{DIAS}$. Pulsatile skull expansion $\Delta$x can be measured using system 20. For example, a representative output of system 20 is illustrated in FIG. 5 where phase difference is measured in terms of an output voltage. Note that in tests of the present invention, the phase difference waveform depicted in FIG. 5 correlated well with the patient's pulse waveform. Accordingly, a peak-to-valley measurement of the waveform in FIG. 5 is indicative of pulsatile skull expansion $\Delta$x. The conversion of a peak-to-valley voltage to a pulsatile skull expansion $\Delta$x is made possible by calibration of system 20 as would be understood by one of ordinary skill in the art.

The advantages of the present invention are numerous. Determination of diastolic ICP is determined through the use of easily taken measurements. The process is non-invasive in nature and can, therefore, be used for both one-time and longer term monitoring scenarios. Thus, the present invention will find great utility in both critical and non-critical ICP-related pathologies as well as other medical applications requiring knowledge of diastolic ICP.

Although the invention has been described relative to a specific embodiment thereof, there are numerous variations and modifications that will be readily apparent to those skilled in the art in light of the above teachings. For example, rather than using the tilt bed approach to causing known changes in ICP, system 20 could be used to apply incremental increases in headband pressure to bring about changes in path length to permit calibration. It is therefore to be understood that, within the scope of the appended claims, the invention may be practiced other than as specifically described.

What is claimed as new and desired to be secured by Letters Patent of the United States is:

1. A method of determining diastolic intracranial pressure (ICP) in a patient, comprising the steps of:
    measuring a first change in the length of a path across the skull of the patient caused by a known change in ICP in the patient, wherein said first change in the length of said path relative to said known change in ICP is indicative of an elasticity constant for the patient; and
    measuring a second change in the length of said path occurring between systolic and diastolic portions of a heartbeat of the patient, wherein a diastolic ICP is a function of said elasticity constant and said second change in the length of said path.

2. A method according to claim 1 wherein each of said steps of measuring comprises the steps of:
    coupling an acoustic signal to a first location on the patient's skin adjacent the skull of the patient;
    detecting said acoustic signal at a second location on the patient's skin adjacent the skull of the patient; and
    measuring a phase difference between said acoustic signal so-coupled at said first location and said acoustic signal so-detected at said second location, wherein said phase difference is indicative of one of said first change and said second change.

3. A method according to claim 2 further comprising the step of applying pressure to the patient's skin at each of said first location and said second location prior to said steps of coupling and detecting, wherein pulsatile blood perfusion at said first location and said second location is reduced.

4. A method according to claim 2 wherein said first location and said second location are approximately diametrically-opposed to one another on either side of the skull of the patient.

5. A method according to claim 2 wherein said first location and said second location are approximately the same location.

6. A method according to claim 1 wherein said known change in ICP is induced by the step of manipulating the patient in a mechanical fashion.

7. A method according to claim 1 wherein said known change in ICP is induced by the step of manipulating the patient in a chemical fashion.

8. A method of determining diastolic ICP in a patient, comprising the steps of:
    measuring a first change $\Delta l$ in the length of a path across the skull of the patient caused by a known change $\Delta ICP$ in ICP in the patient, wherein $\Delta ICP/\Delta l$ defines an elasticity constant K for the patient; and
    measuring a second change $\Delta x$ in the length of said path occurring between systolic and diastolic portions of a heartbeat of the patient, wherein a diastolic ICP is equal to $A(K\Delta x)^B$, where A and B are constants derived from a data relationship between pulsatile variations in ICP and a mean diastolic ICP, wherein said data relationship is defined for a general human population.

9. A method according to claim 8 wherein each of said steps of measuring comprises the steps of:
    coupling an acoustic signal to a first location on the patient's skin adjacent the skull of the patient;
    detecting said acoustic signal at a second location on the patient's skin adjacent the skull of the patient; and
    measuring a phase difference between said acoustic signal so-coupled at said first location and said acoustic signal so-detected at said second location, wherein said phase difference is indicative of one of said first change and said second change.

10. A method according to claim 9 further comprising the step of applying pressure to the patient's skin at each of said first location and said second location prior to said steps of coupling and detecting, wherein pulsatile blood perfusion at said first location and said second location is reduced.

11. A method according to claim 9 wherein said first location and said second location are approximately diametrically-opposed to one another on either side of the skull of the patient.

12. A method according to claim 9 wherein said first location and said second location are approximately the same location.

13. A method according to claim 8 wherein said known change in ICP is induced by the step of manipulating the patient in a mechanical fashion.

14. A method according to claim 8 wherein said known change in ICP is induced by the step of manipulating the patient in a chemical fashion.

15. A method of determining diastolic ICP in a patient, comprising the steps of:
    coupling an acoustic signal to a first location on the patient's skin adjacent the skull of the patient;
    detecting said acoustic signal at a second location on the patient's skin adjacent the skull of the patient;
    inducing a known change in ICP in the patient;
    measuring a first phase difference between said acoustic signal so-coupled at said first location and said acoustic signal so-detected at said second location, said first phase difference being caused by said known change in ICP, wherein said first phase difference is indicative of a first change in the length of a path across the skull of the patient, and wherein said first change in the length of said path relative to said known change in ICP is indicative of an elasticity constant for the patient;
    repeating said steps of coupling and detecting; and
    measuring, during said step of repeating, a second phase difference between said acoustic signal so-coupled at said first location and said acoustic signal so-detected at said second location, said second phase difference occurring between systolic and diastolic portions of a heartbeat of the patient, wherein said second phase difference is indicative of a second change in the length of said path occurring between said systolic and diastolic portions, wherein a diastolic ICP is a function of said elasticity constant and said second change in the length of said path.

16. A method according to claim 15 further comprising the step of applying pressure to the patient's skin at each of said first location and said second location prior to said steps of coupling and detecting, wherein pulsatile blood perfusion at said first location and said second location is reduced.

17. A method according to claim 15 wherein said first location and said second location are approximately diametrically-opposed to one another on either side of the skull of the patient.

18. A method according to claim 15 wherein said first location and said second location are approximately the same location.

19. A method according to claim 15 wherein said known change in ICP is induced by the step of manipulating the patient in a mechanical fashion.

20. A method according to claim 15 wherein said known change in ICP is induced by the step of manipulating the patient in a chemical fashion.

* * * * *